United States Patent
Amin et al.

(10) Patent No.: US 11,564,877 B2
(45) Date of Patent: Jan. 31, 2023

(54) RESPONSIVE COATINGS FOR HAIR FIBERS

(71) Applicants: L'OREAL, Paris (FR); MASSACHUSETTS INSTITUTE OF TECHNOLOGY, Cambridge, MA (US)

(72) Inventors: Samiul Amin, Clark, NJ (US); Niels Holten-Andersen, Quincy, MA (US); Bavand Keshavarz, Cambridge, MA (US); Gareth H. McKinley, Cambridge, MA (US); Sivaramakrishnan Muthukrishnan, Acton, MA (US); Brady Zarket, Union, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/600,233

(22) Filed: Oct. 11, 2019

(65) Prior Publication Data

US 2020/0113809 A1    Apr. 16, 2020

Related U.S. Application Data

(60) Provisional application No. 62/744,923, filed on Oct. 12, 2018.

(51) Int. Cl.
*A61K 8/86* (2006.01)
*A61K 8/44* (2006.01)
*A61K 8/64* (2006.01)

(52) U.S. Cl.
CPC .............. *A61K 8/86* (2013.01); *A61K 8/44* (2013.01); *A61K 8/64* (2013.01); *A61K 2800/58* (2013.01); *A61K 2800/884* (2013.01)

(58) Field of Classification Search
CPC ........ A61K 2800/58; A61K 8/44; A61K 8/64; A61K 2800/884; A61Q 5/04; A61Q 5/06
See application file for complete search history.

(56) References Cited

U.S. PATENT DOCUMENTS

| | | | |
|---|---|---|---|
| 3,973,574 A * | 8/1976 | Minagawa | A45D 7/04 132/204 |
| 5,294,230 A * | 3/1994 | Wu | A61Q 5/04 132/203 |
| 7,622,533 B2 | 11/2009 | Lee | |
| 8,409,602 B2 | 4/2013 | Messersmith et al. | |
| 8,673,286 B2 | 3/2014 | Messersmith et al. | |
| 8,796,394 B2 | 8/2014 | Messersmith et al. | |
| 8,815,793 B2 | 8/2014 | Messersmith et al. | |
| 8,916,652 B2 | 12/2014 | Dalsin et al. | |
| 9,259,473 B2 | 2/2016 | Messersmith et al. | |
| 9,320,826 B2 | 4/2016 | Lee et al. | |
| 9,572,910 B2 | 2/2017 | Messersmith et al. | |
| 9,687,582 B2 | 6/2017 | Messersmith et al. | |
| 2008/0299059 A1 | 12/2008 | Quadir | |
| 2011/0077216 A1 | 3/2011 | Kastrup et al. | |
| 2012/0003888 A1 | 1/2012 | Lee et al. | |
| 2012/0012129 A1 * | 1/2012 | Hagenow | A61K 8/22 132/208 |
| 2013/0053594 A1 | 2/2013 | Lee et al. | |
| 2017/0296450 A1 | 10/2017 | Brody et al. | |

FOREIGN PATENT DOCUMENTS

| | | | |
|---|---|---|---|
| EP | 1651313 B1 | 4/2009 | |
| KR | 20080058134 A | 6/2008 | |
| KR | 20120063753 A | 6/2012 | |
| WO | 2010091300 A1 | 8/2010 | |
| WO | WO-2016044582 A1 * | 3/2016 | A61K 8/8164 |
| WO | 2018183284 A1 | 10/2018 | |

OTHER PUBLICATIONS

Xiaoping Zeng, et al, Synthesis and Characterization of DOPA-PEG Conjugates, 2000, Polymer Preprints, 41(1), 989.

Matthew S. Menyo, et al., Versatile tuning of supramolecular hydrogels through metal complexation of oxidation-resistant catechol-inspired ligands, 2013.

PCT Notification of Transmittal of the International Search Report and the Written Opinion of the International Searching Authority, issued to PCT Application No. PCT/US2019/055962 dated Jan. 3, 2020.

Neils Holten-Anderson, et al., pH induced metal-ligand cross-links inspired by mussel yield self-healing polymer networks with near-covalent elastic moduli, Feb. 15, 2011, PNAS, vol. 108, No. 7, 2651-2655.

Akram Yasin, et al., A shape memory hydrogel induced by the interactions between metal ions and phosphate, The Royal Society of Chemistry, Soft Matter, Paper, 2014, 10. 972-977.

Bavand Keshavarz, et al., Probing the rehological properties of natural and synthetic fibers with a simple torsional pendulum, L'Oreal Research & Innovation, 90th Annual Meeting of the Society of Rheology, Houston Texas.

(Continued)

*Primary Examiner* — Andrew S Rosenthal
*Assistant Examiner* — Lyndsey M Beckhardt
(74) *Attorney, Agent, or Firm* — McNees Wallace & Nurick LLC

(57) ABSTRACT

Cosmetic compositions, systems and methods for conferring responsive durable shaping of keratinous fibers employ at least one shape memory polymer that includes a four-armed branched polyethylene glycol (PEG) based polymer that is functionalized with one or more metal-coordination active groups. The shape memory polymer forms a crosslinked network coating on a substrate, for example a substrate selected from keratinous substrates, for example, hair. Hair coated with the shape memory polymer and treated with an oxidizing agent can be shaped, locked into shape, and reprogrammed by modulation of pH. The coated hair retains durable shaping properties through at least one shampoo treatment. The cosmetic compositions, systems and methods provide durable and reprogrammable durable shaping of the keratinous substrate, for example for styling hair.

20 Claims, 6 Drawing Sheets

(56) References Cited

OTHER PUBLICATIONS

Meng Shan, et al., A pH, Gluecose, and Dopamine Triple-responsive, Self-healable Adhesive Hydrogel Formed by Phenylborate-Catechol Complexation, 2012.

* cited by examiner

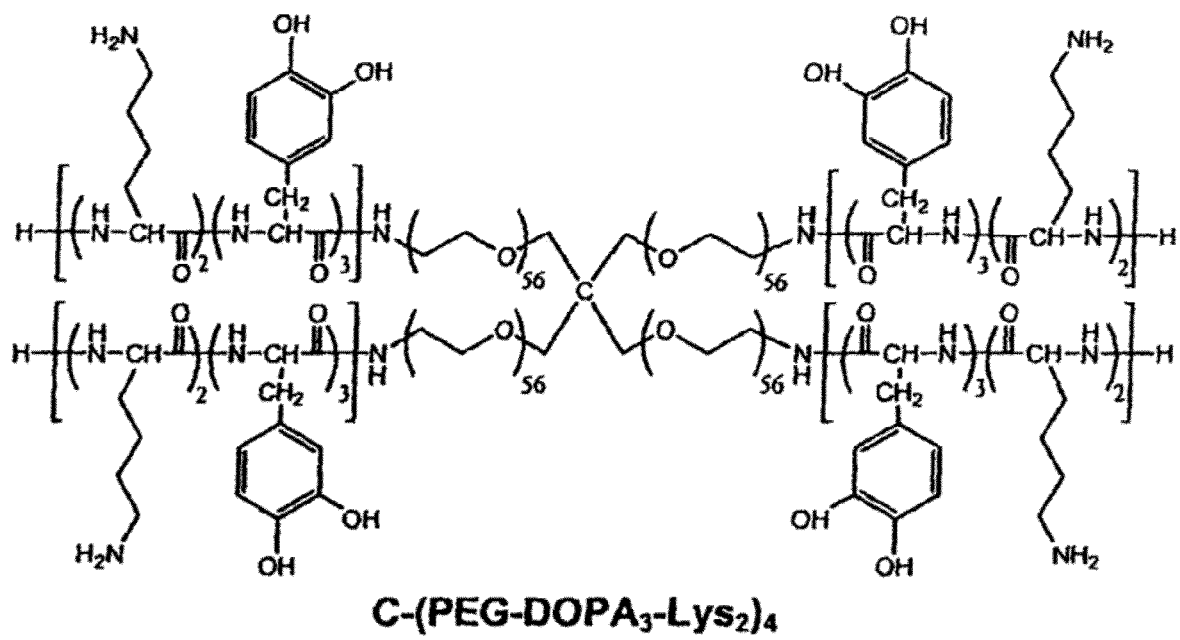
C-(PEG-DOPA$_3$-Lys$_2$)$_4$
PEG 10K – (DL)$_4$
(C)
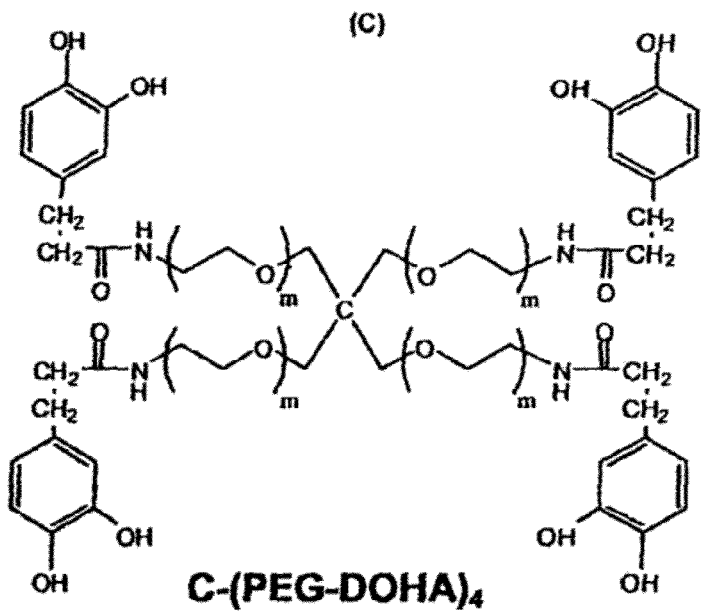
C-(PEG-DOHA)$_4$
(d) PEG 10K – (DH)$_4$ m=56
(g) PEG 20K – (DH)$_4$ m=113
FIG 1 (continued)

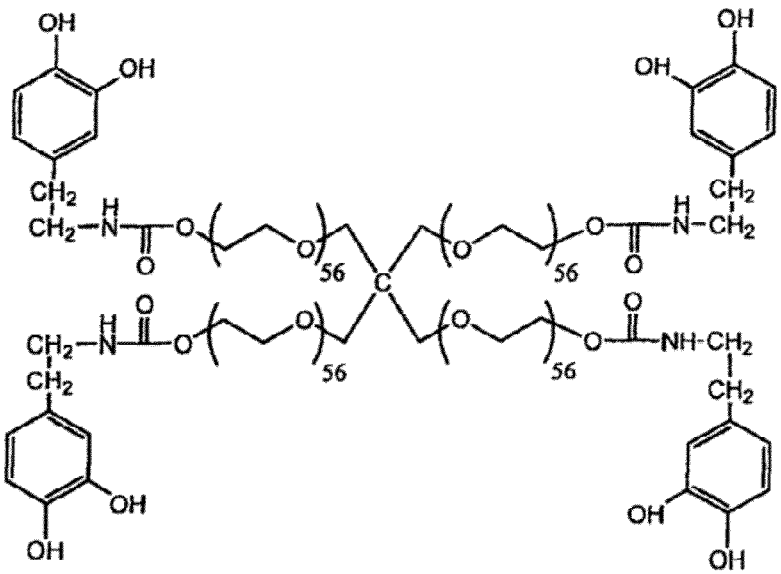
C-(PEG-DMu)₄
PEG 10K – (DMu)₄
(e)
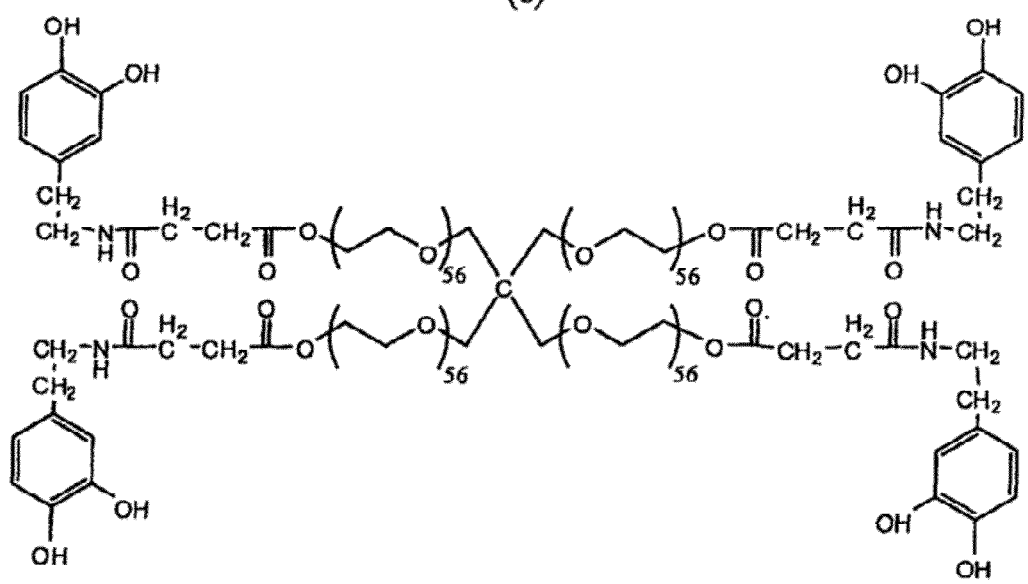
C-(PEG-DMe)₄
PEG 10K – (DMe)₄
(f)
FIG 1 (continued)

RESPONSIVE COATINGS FOR HAIR FIBERS

PRIORITY

This application is a United States Non-Provisional Patent Application and claims the benefit under 35 U.S.C. § 119(e) to U.S. Provisional Application Ser. No. 62/744,923 filed Oct. 12, 2018, the entirety of which application is incorporated herein by reference.

FIELD OF THE INVENTION

The present invention generally relates to compositions, systems and methods for conferring durable shaping of keratinous fibers. More particularly, the present invention relates to cosmetic treatment compositions, systems and methods that include a shape memory polymer that forms a crosslinked network coating on keratinous substrates and can be shaped, locked and reprogrammed by modulation of pH. The cosmetic treatment system and method provide durable and reprogrammable durable shaping of the keratinous substrate, for example for styling hair.

BACKGROUND OF THE INVENTION

In the area of hair care there is a wide variety of hair styling products that can be used to impart shape or style to the hair and/or to help maintain a particular hair style. The goals of many hair styling compositions include to hold or fix the hair in a particular shape, to impart or increase volume of the hair, to smooth the hair, and to impart resistance to humidity and mechanical alteration of the imparted shape.

There are a variety of products that provide permanent shape control that withstands washing and mechanical forces to retain shape. There are also many products that confer temporary shape control providing the flexibility of non-permanent hairstyles and avoiding many of the damaging effects of permanent shaping products. Methods for non-permanent shaping of keratinous fibers include, for example, brushing, teasing, braiding, the use of hair rollers, and heat styling, optionally with a commercially available styling product. Some examples of heat styling include blow drying, crimping, curling, and straightening methods using elevated temperatures (such as, for example, setting hair in curlers and heating, and curling with a curling iron and/or hot/steam rollers and/or flat iron). Typically, such non-permanent styles disappear when the hair is wetted, especially when the hair is washed with water and/or shampoo or when the hair is exposed to high humidity conditions, wind or other mechanical alteration of the style. There is a need, therefore, for compositions and methods for non-permanent shape control that result in durable or longer lasting shape or style even when the styled/shaped/curled hair is exposed to adverse environmental and physical factors and/or when wetted, washed, or shampooed.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In accordance with a first embodiment, provided is a system and method for treating keratinous substrates such as hair. In various embodiments, the system includes:

(a) an adhering composition that includes (i) at least one polyethylene glycol (PEG) based polymer that is functionalized with one or more metal-coordination active groups and (ii) a cosmetically acceptable carrier having an acidic to neutral pH;

(b) a setting composition that includes (i) a metallic coordination agent in (ii) a cosmetically acceptable carrier having an acidic to neutral pH, and (c) a fixing composition that includes (i) a cosmetically acceptable carrier having a pH that is greater than the pH of the setting composition by at least Δ pH=1, in some embodiments, an alkaline pH.

In some embodiments the PEG based polymer is four-armed. In other embodiments, the PEG based polymer is two armed, and unbranched. The shape memory polymer is characterized as being capable of forming a crosslinked network by initial polymerization of shape memory polymer monomer units. In accordance with the various embodiments, the system further includes an oxidizing agent that is present in one or more of (a) the adhering composition, (b) setting composition, and a sub-composition, (a'). The cosmetic treatment system provides durable and reprogrammable durable shaping of the keratinous substrate, for example for styling hair. In some embodiments, the system further includes (e) a resetting composition that includes at least one chelating agent, an acidic to neutral pH, or a combination of these.

In accordance with a second embodiment, provided is a method for treating keratinous substrates, such as hair, using compositions as described herein, for example including but not limited to the compositions of the above-described system. The method includes application of compositions described herein to the keratinous substrate, such as the cuticle of hair fibers, in a step wise fashion. In accordance with the various embodiments of the method, the steps including a multi-step process including two, three or more steps, and combinations of these. In accordance with the various embodiments, additional steps may include, by way of example only, one or more of styling, heat styling, rinsing, drying, and heating, in various combinations and in various orders relative to the application steps. And in some embodiments, the method includes additional steps comprising repeating at least one or more of the adhering, setting and fixing steps in a forward or backward order relative to the initial steps, so as to re-set or reprogram the shaping of the keratinous substrate imparted by styling.

In accordance with a third embodiment, provided is an article of manufacture for cosmetic treatment of keratinous substrates, such as keratinous fibers, comprising packaging that includes separate receptacles each of which contains compositions as described herein, for example including but not limited to the compositions of the various embodiments of the above-described system. In accordance such embodiments, the system includes separate receptacles of each of the compositions of the inventive system. The article of manufacture may be a kit.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
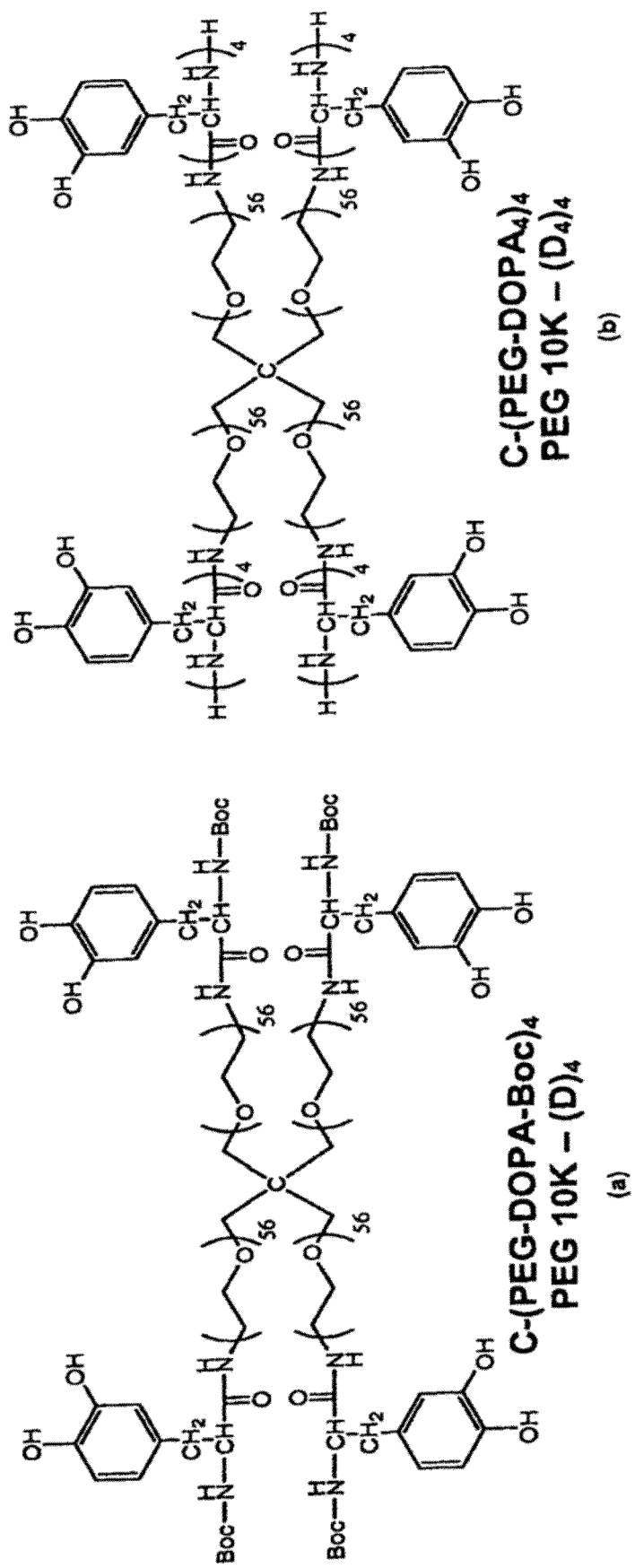
FIG. 1 shows alternate embodiments of shape memory polymers that may be used in accordance with the disclosure (from U.S. Pat. No. 8,673,286)

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

"Active material" as used herein with respect to the percent amount of an ingredient or raw material, refers to 100% activity of the ingredient or raw material.

"Applying a composition onto keratin fibers" and "applying a composition onto hair" and "treating keratinous fibers" and variations of these phrases as used herein are intended to mean contacting the fibers or hair, with at least one of the compositions of the invention, in any manner.

"Chelating agent" as used herein means and refers to a compound or ligand that can bind to a metal ion (a metallic coordination agent), usually through more than one ligand atom, to form a chelate. See Lewis, R. J., Hawley's Condensed Chemical Dictionary p. 240 (1997). A chelate is usually a type of coordination compound in which a central metal ion such as $Co^{2+}$, $Ni^{2+}$, $Cu^{2+}$, $Ca^{2+}$ or $Zn^{2+}$ is attached by coordinate links to two or more nonmetal atoms, i.e., ligands, in the same molecule. Common chelating agents include ethylene-diaminetetraacetic acid (EDTA), nitrilotriacetic acid, and ethylenegylcol-bis(β-amino-ethyl ether)-N,N-tetraacetic acid.

"Carrier" and "Cosmetically acceptable carrier" as used herein means and refers to one or more cosmetically acceptable ingredients useful in solubilizing, dispersing or delivering the compositions at the appropriate pH.

"Durable retention of a shape" as used herein means that, following at least one of wetting/shampoo/washing/rinsing, exposure to high humidity conditions and mechanical alteration after treatment of keratinous fibers such as hair with the compositions of the present disclosure, treated hair still exhibits the ability to retain a particular or desirable shape after styling as compared to the exhibited ability of untreated hair to retain a particular or desirable shape after styling. And "durable shaping" as used herein refers to holding or keeping a shape of a keratinous fiber until the keratinous fiber is washed with water and/or shampoo or exposed to high humidity conditions. Retention of a shape can be evaluated by measuring, and comparing, the ability to retain a curl under conditions of high relative humidity of the treated hair and of the untreated hair in terms of Curl Efficiency.

"Hair styling composition" or more simply "composition" as used herein means and refers to a mixture of ingredients that can be used to affect, create or maintain a hairstyle, in various product forms, for example, sprays, mousses, gels, and the like.

"Heat-activated" composition as used herein refers to a composition which, for example, shapes the at least one keratinous fiber in an enhanced manner as compared with the same composition which is not heated during or after application of the composition. Another example includes a composition which retains a shape of at least one keratinous fiber in an enhanced manner as compared with the same composition which is not heated during or after application. And "heating" as used herein refers to the use of elevated temperature (i.e., above room temperature such as above 40° C.). In one embodiment, the heating in the inventive method may be provided by directly contacting the at least one keratinous fiber with a heat source, e.g., by heat styling of the at least one keratinous fiber. Non-limiting examples of heat styling by direct contact with the at least one keratinous fiber include flat ironing and curling methods using elevated temperatures (such as, for example, setting hair in curlers and heating, and curling with a curling iron and/or hot rollers). In another embodiment, the heating in the inventive method may be provided by heating the at least one keratinous fiber with a heat source which may not directly contact the at least one keratinous fiber. Non-limiting examples of heat sources which may not directly contact the at least one keratinous fiber include blow dryers, curling irons, curling brushes, flat irons, hot rollers, hood dryers, heating caps and steamers.

"Keratinous substrate" as used herein also includes "keratinous tissue" or "keratinous fibers," which as defined herein, may be human keratinous fibers, and may be chosen from, for example, hair, such as hair on the human head, or hair comprising of eyelashes or hair on the body.

"Metal coordination chemistry" as used herein means and refers to the various metals and ligands that participate in coordination complexes that comprise one or more central atoms or ions, typically metal ions (metallic coordination agents), with one or more attached ligands, where the total number of attachments between the central metal and the ligands is the coordination number. Under some conditions, the metal and ligands associate in the absence of covalent bonds, and under certain conditions, the ligands attach to the metal via coordinate covalent bonds, wherein the electrons of the bond are derived from the ligand. Metal coordination active groups are present on the PEG-based polymers herein to provide shape memory polymers, as used herein, and participate as ligands that interact with metallic coordination agents to form coordination complexes. Chelating agents are ligands that associate with metallic coordination agents and can disrupt coordination complexes formed among metallic coordination agents and shape memory polymers as used herein.

"Reprogrammable" as used herein means and refers to the property of retention of an initial shape styling achieved by use of the inventive system and method whereby keratinous fibers are treated and locked. The initially treated keratinous fibers may thereafter be wetted or washed, restyled and locked at a pH that is greater than the pH of the setting composition by at least $\Delta$ pH=1 (in some embodiments, an alkaline pH) and upon application of resetting treatment (acid pH and/or chelators) will recover to the initially locked style.

"Shape memory polymer" as used herein refers to the components of the system that form crosslinked networks when applied to keratinous substrates and are activated by modulation of pH in the presence of metal ions (metallic coordination agents) to form coatings that are responsive to shaping by any styling method. The shape memory polymers are polyethylene glycol (PEG) based polymers functionalized with one or more metal coordinate active groups and optional terminal peptides as protective groups. Thus, the shape memory polymers generally include a central atom to which is bonded directly or indirectly to PEG-based polymer arms, each arm including a PEG structure bonded directly or indirectly to at least one catechol-like moiety as a metal coordination active group, the metal coordination active group bonded directly or indirectly to an optional protective terminal peptide. As described herein, representative examples of shape memory polymers have four PEG-based polymer arms, each arm including one metal coordination active group, which constitutes a monomer unit of the shape memory polymer. Shape memory polymer monomer units crosslink under oxidizing conditions to form a polymer network that can be further crosslinked in the presence of metallic coordination agents modulated by pH.

"Style" and/or "Styling" as used herein includes shaping, straightening, curling, or placing a keratin fiber such as hair, in a particular arrangement, form or configuration; or altering the curvature of a keratinous fiber or other substrate; or re-positioning a keratin fiber or other substrate to a different arrangement, form or configuration; or providing/maintaining a hold to the shape or configuration of the keratin fiber. In some embodiments, the hold to the shape of configuration of the fiber may be expressed as an improved bending force property. And "styling keratinous fibers" and variations thereof as used herein are understood to refer to any means or method of modifying the appearance of the keratinous fibers or the hair with respect to their spatial arrangement or configuration or curvature or form. When the keratinous fibers comprise hair on the human head, the term "styling keratinous fibers" or "styling hair" is also understood to include curling or waving or embossing the hair or smoothing or straightening the hair or spiking the hair or providing/maintaining a hold to the shape or configuration of the keratin fiber.

"Treat" (and its grammatical variations) as used herein refers to the application of the compositions of the present invention onto keratinous substrates such as keratinous fibers or hair or skin.

"Wash cycle" as used herein, refers to a step or process of washing a keratinous substrate and may include treating the substrate with a surfactant-based product (e.g., shampoo or conditioner or body wash) then washing or rinsing the substrate with water. The term "wash cycle" may also include washing or rinsing the substrate with water.

System and Method

This invention relates to a system and method for extended term durable shaping of hair using a shape memory polymer system that is modulated by pH and includes a metal coordination system. An exemplified shape memory polymer is a four-armed branched polyethylene glycol-based polymer that is functionalized with metal-coordination active groups that include catechol or catechol-like moieties, the shape memory polymer provided in a composition that includes a carrier suitable for application to hair. The pH of the compositions may be modulated to modulate the coordination (binding interaction) of a metallic coordination agent with metal-coordination sites on the shape memory polymer.

The inventors are the first to describe a system for imparting reprogrammable durable shaping of keratinous substrates that comprises a shape memory polymer provided at an acidic pH that is applied first to the hair, in some embodiments including application of a fixing composition that a pH that is greater than the pH of the shape memory polymer composition by at least $\Delta$ pH=1. The fixing composition locks the shape of a crosslinked network of the shape memory polymer coated on keratinous fibers.

It has been surprisingly and unexpectedly discovered by the inventors that the novel compositions of the shape memory system as described herein, when applied to keratinous substrates such as hair, can impart lasting non-permanent and durable styling or shaping benefits to the substrates. The system enhances the properties of the hair, such as with respect to humidity resistance, water resistance, mechanical resistance, chemical resistance, and hydrophobicity. It has also been surprisingly and unexpectedly discovered that the shaping benefits conferred by the system used according to the method hereof, in various embodiments, are semi-permanent and durable in that they are retained through at least one wash cycle without the requirement for retreatment. In some embodiments, the effect is retained through up to or more than three wash cycles. For example, treatment of hair even without use of the fixing composition provides a durable network of crosslinked polymer on the hair that can be reshaped and can be subject to shaping and/or shampooing prior to or after application of the fixing composition.

The inventors have observed that keratinous fibers that are first treated according to the invention to confer a fixed styling may be restyled with or without shampooing and then returned to the initial fixed styling without complete or appreciable loss of the initial style. The inventors have also surprisingly observed that through at least one wash cycle, the reprogrammable shape memory is preserved. Once the reprogrammable shape memory is lost, retreatment may be employed to confer a fresh reprogrammable shaping that is resistant to further wash cycles.

System and Method

In accordance with the various embodiments, the system includes:
(a) an adhering composition that includes (i) at least one shape memory polymer comprising a polyethylene glycol (PEG) based polymer that is functionalized with one or more metal-coordination active groups and (ii) a cosmetically acceptable carrier having an acidic to neutral pH;
(b) a setting composition that includes (i) a metallic coordination agent in (ii) a cosmetically acceptable carrier having an acidic to neutral pH, and
(c) a fixing composition that includes (i) a cosmetically acceptable carrier having a pH that is greater than the pH of the setting composition by at least $\Delta$ pH=1 (in some embodiments, an alkaline pH).

The shape memory polymer is characterized as being capable of forming a crosslinked network by initial polymerization of shape memory polymer monomer units. In accordance with the various embodiments, the system further includes an oxidizing agent that is present in one or more of (i) (a) the adhering composition, (ii) the setting composition, and (iii) a sub-composition, (a'). The cosmetic treatment system provides durable and reprogrammable durable shaping of the keratinous substrate, for example for styling hair. In some embodiments, the system further includes (e) a resetting composition that includes at least one chelating agent, an acidic to neutral pH, or a combination of these.

The system and method provided according the various embodiments generally rely on the chemical interaction of certain of the various components of the compositions via a metal coordination system. The metal coordination system is formed at least by interaction of the polyethylene glycol (PEG) based polymer and the metal coordination active groups (which together form the shape memory polymer). Application of the compositions of the system to a keratinous fiber enables the metal coordination active groups to serve as ligands that bind with a subsequently added metallic coordination agent to form a durable shape responsive coating comprising complex interconnected/crosslinked monomer units of polyethylene glycol (PEG) based polymers that are complexed with the metal via the coordination active groups. The formed coating is shapeable when maintained at relatively low pH and can be reversibly "locked" or fixed when exposed to relatively high pH. According to the various embodiments, the total number of attachments between the metal and the ligands is referred to as the coordination number and corresponds with the number of metal coordination active groups that are bonded to the polyethylene glycol (PEG) based polymer.

The compositions of the system are characterized as having a pH within the ranges as disclosed herein, wherein each of the adhering and setting compositions are provided at an acidic or neutral pH, the fixing composition is provided at a pH that is greater than the pH of the setting composition by at least $\Delta$ pH=1 (in some embodiments, an alkaline pH), and the resetting composition is provided, in some embodiments, at an acidic to neutral pH or alternatively comprising a molar excess of chelating agent in an acidic to neutral pH. As further described herein, acidic to neutral pH means and includes a pH ranging from about 3 to about 7, or from about 3 to about 6, and alkaline pH means and includes a pH ranging from 7.5 to about 13, or from about 8 to about 11, or from about 8.5 to about 9. It will be appreciated that while the ranges as provided above represent what is generally considered to characterized acidic, neutral and alkaline, the principal of operation of the invention is dependent on the change between pH of the various compositions. And it will further be appreciated that depending on the specific coordination chemistries employed, for example the specific catechol or catechol-like groups and the specific metallic coordination agents used, the exact ranges of pH associated with each of acidic and basic may vary. Thus, while the exemplified embodiments herein operate in the pH ranges as recited above, wherein the setting, fixing and resetting pH values correspond to the above ranges, the operation of the metal coordination chemistry is reliant on the differences between the pH values of the compositions, not the precise pH ranges as described. In the various embodiments, each of the compositions hereof that differ in pH have a pH that is either greater than or less than the pH of another of the compositions by at least $\Delta$ pH=1.

In accordance with the various embodiments of the method, the compositions of the system are applied sequentially, in a fixed order to achieve non-permanent and durable shaping. In an embodiment of the invention that constitutes the core method, the steps include sequential application of the compositions as described above further including styling and optional drying and heating steps. In some specific embodiments of the method, additional steps including repetition of any one or more steps of the core method, in forward or reverse order, may be followed to one or more of reverse, revise, reset or reinforce the achieved according to the core method.

In accordance with some embodiments, the method includes a one step process wherein an adhering composition is applied to the keratinous substrate and subjected to oxidizing conditions to form a crosslinked polymer network on the substrate. In accordance with some embodiments, the method includes a two-step process wherein following application of the adhering composition, a setting composition is applied to the substrate. In accordance with some embodiments, the method includes a three-step application process, wherein each of adhering, setting and fixing compositions are applied to the keratinous substrate in a step-wise fashion to treat the substrate. In such embodiments, additional steps may include, by way of example only, one or more of styling, heat styling, rinsing, drying, and heating, in various combinations and in various orders relative to the application steps. And in some embodiments, the method includes additional steps comprising repeating at least one or more of the adhering, setting and fixing steps in a forward or backward order relative to the initial steps, so as to re-set or reprogram the shaping of the keratinous substrate imparted by styling. In accordance with some embodiments, the method includes application of a resetting composition that is provided at an acidic to neutral pH and/or includes chelating agents sufficient to sequester metallic coordination agents from association with the shape memory polymer to enable reshaping.

The method includes the steps of adhering a layer of networked shape memory polymer on keratinous fibers, the adhering including crosslinking, for example by chemical or energy driven crosslinking of the monomer units of the shape memory polymer, followed by at least setting the layer of the adhering polymer network on the keratinous fibers followed by fixing the set layer on the keratinous fibers. Adhering refers to mechanical coating of the adhering composition on the keratinous substrate. Setting refers to initial and largely non-covalent crosslinking between the coordination active groups of the shape memory polymer and a metallic coordination agent added as a metal ion and/or functioning as metallic oxidizing agent that also drives polymerization of the monomers. In a set state, the polymer forms a network that is loosely associated with the metallic coordination agent. Fixing is achieved by adjustment of the pH by application of the fixing composition having a pH that is greater than the pH of the setting composition by at least $\Delta$ pH=1 (in some embodiments, an alkaline pH). Fixing refers to covalent crosslinking between the metal and coordination active group ligands with the metal. According to the methods, the keratinous fibers are subjected to the desired styling, with or without the addition of heating, to achieve the desired style.

More specifically, use of the system according to the method includes application in acidic conditions of a coating layer of the shape memory polymer onto the hair which is in one of its natural state or an initial predetermined shape (e.g. straight or curly hair), whereby the coating initially covers the surface of the hair and is retained on the hair by operation of crosslinking that occurs between monomer units of the shape memory polymer to form a shape memory polymer network, followed by application in acidic conditions of a metallic coordination agent. According to the method, the hair may then be treated with a fixing composition at elevated pH to lock the style. Or the hair may then be restyled in a different way, such as to straighten curly hair, or impart a specifically desired extent of curl to the hair. In a second step, a metallic coordination agent applied to the hair sets the new shape. Thereafter, in a third step, treatment with a fixing composition at a pH that is greater than the pH of the setting composition by at least $\Delta$ pH=1 (in some embodiments, an alkaline pH) shifts the pH of the set coating from acidic to neutral to a pH that is greater than the pH of the setting composition by at least $\Delta$ pH=1 (according to some exemplified embodiments a pH of ~8), whereby most of the metals are coordinated with a maximum number of ligands (in some examples, 2 or more coordination active sites). At this state the modulus of the gelled coating is increased, "locking" the temporary shape in place.

In some embodiments, a step of resetting or relaxing the fixed shape is achieved by adding a resetting composition characterized as one or more of having an acidic to neutral pH, and comprising an excess of one or more chelating agents, which chemically alters the bonding between the metal and ligands to return the adhered shape memory polymer network to a set, non-crosslinked state. Thus, to achieve reprogramming, fixed keratinous fibers are treated with a resetting composition, which may be preceded or accompanied by one of wetting or shampooing. The keratinous fibers are thus returned to an essentially set state and may be subsequently styled and fixed.

Upon the application of a resetting or relaxing composition that includes one or more of a metal chelating agent or acidic buffer, the coating recovers some of the initial shape and may be restyled followed by application of the fixing composition. The inventors have observed that the coating of networked polymer is retained on the hair for at least three wash cycles and can be restyled by use of metal chelating agent and/or acidic treatment followed by reapplication of one or more of oxidizing agents, metallic coordination agent and increased pH, as described herein.

It will be appreciated that the method may be carried out with the addition of intervening steps such as drying, heating, application of other treatments (products), wetting, shampooing, and the like, in any combination and in any order. According to some embodiments the methods, may include reapplication of one or more components of the system, either before or after or in the absence of one or more wash cycles. In some specific embodiments, restyling may be achieved after the core method is applied by reapplication of one or more of the resetting, setting and fixing compositions.

System Compositions

Adhering Composition

Adhering Compositions according to the disclosure comprise at least one shape memory polymer comprising a polyethylene glycol (PEG) based polymer that is functionalized with one or more metal-coordination active groups and a carrier.

Shape Memory Polymer

In accordance with the disclosure, shape memory polymers comprise a polyethylene glycol (PEG) based polymer that is functionalized with one or more metal-coordination active groups. The PEG-based polymers are four-armed branched, wherein each branch comprises polyethylene glycol that is functionalized with metal-coordination active groups that include catechol or catechol-like moieties for application to hair. Each branch may comprise other moieties and linkers in addition to PEG and the metal-coordination active groups.

In accordance with the various embodiments, the shape memory polymer is prepared with at least one metal coordination active group on each of its arms, though in some embodiments, more or fewer coordination sites may be used. Each coordination site serves as a ligand for binding interaction with a metal ion. In one example of a metal coordination system in which the metal ion can bind with up to three metal coordination sites/ligands, most metal ions will be associated with only one ligand at acidic pH, and at neutral pH the metal ion will coordinate with two ligands on the polymer, and at a basic pH, the metal ion will coordinate with three ligands on the polymer. The consequence of this change in coordination activity is a change in the viscoelastic properties of the shape memory polymer, which when applied to keratinous fibers, such as hair, elicits a shape-memory effect.

In exemplary embodiments, the shape memory polymer includes one metal-coordination active group per branch, for a total of four metal-coordination active groups per shape memory polymer. In a particular embodiment, the metal coordination active groups comprise L-3-4-dihydroxyphenylalanine (DOPA), and an exemplary shape memory polymer is a four-armed branched polymer, each branch comprising polyethylene glycol end functionalized with DOPA-based amino acid. Of course, it will be appreciated that more or fewer coordination sites may be used. Moreover, while the exemplary embodiment includes chatechol like coordination groups comprising DOPA, other coordination groups may be selected, and the shape memory polymers may be formed with homogenous or heterogenous coordination groups.

In various embodiments, the at least one polyethylene glycol (PEG) based shape memory polymer comprising a four-armed branched polyethylene glycol (PEG) based polymer comprises on each arm a metal-coordination active group comprising a DOPA-based amino acid and a short peptide. The shape memory polymer may be represented by the formula: $Z(PEG_l\text{-}MCAG_m\text{-}X_n)_4$; wherein Z is a central atom or moiety=one of C (carbon), O (oxygen), S (sulfur), and N (nitrogen), or an atom or a moiety comprising one of C (carbon), O (oxygen), S (sulfur), and N (nitrogen); PEG=a polyethylene glycol for which l>1=1; MCAG=metal coordination active group for which m>1=1; and X=short peptide for which n=0-$\rightarrow$1=1. The shape memory polymer may include one or more additional linking groups between each of the central atom/moiety, PEG, MCAG and X. In some particular embodiments, the shape memory polymer is a PEG-based polymer comprising as the metal coordination active group a DOPA-based amino acid selected from dopamine, 3,4-dihydroxy phenylalanine (DOPA), dihydroxyhydrocinnamic acid, and 3,4-dihydroxyphenyl ethanol and wherein the optional short peptide a short peptide is selected from amino acids with polar side chains which are weakly to strongly basic. Each of the shape memory polymer components including PEG, MCAG may be selected according to the general teaching in the art pertaining to polyethylene glycols, metal coordination active groups such as catechols, for example DOPA, and small peptides. For example, reference may be made to the teachings from U.S. Pat. No. 8,673,286 which teaches a four-armed branched polymer, and to FIG. 1 which shows embodiments of a shape memory polymer according to the disclosure.

As used herein, reference may be made to U.S. Pat. No. 8,673,286, entitled "DOPA-functionalized, branched, poly (aklylene oxide) adhesives" which provides exemplary four-armed shape memory polymers functionalized with one or more metal-coordination active groups on each arm. This reference is incorporated by reference herein in its entirety.

In some exemplary embodiments the shape memory polymer used in accordance with the disclosure is selected from four-armed branched poly(ethylene glycol) (PEG) end-functionalized with a single DOPA (C-(PEG-DOPA-Boc)$_4$), several DOPA residues (C-(PEG-DOPA$_4$)$_4$), a randomly alternating DOPA-lysine peptide (C-(PEG-DOPA$_3$-Lys$_2$)$_4$), a deaminated DOPA, 3,4-dihydroxyhydrocinnamic acid (C-(PEG-DOHA)$_4$), a dopamine through a urethane-linkage (C-(PEG-DMu)$_4$) and dopamine succinamic acid through an ester-linkage (C-(PEG-DMe)$_4$) (as shown in FIG. 1, from U.S. Pat. No. 8,673,286). In other embodiments, the shape memory polymer selected from one of the foregoing wherein the "C" central atom is replaced by one of O, N or S.

In a specific embodiment, the shape memory polymer used in accordance with the discloser is a four-armed branched poly(ethylene glycol) (PEG) end-functionalized with a single DOPA, namely, C-(PEG-DOPA)$_4$. In other embodiments, the shape memory polymer has the foregoing structure, wherein the "C" central atom is replaced by one of O, N or S.

In accordance with the disclosure, each PEG of the shape memory polymer molecule has a molecular weight of between about 1,250 and about 12,500 Dalton. Therefore, it should be understood that the total molecular weight of PEG in the polyethylene glycol (PEG) based polymer (accounting for the PEG portion of each arm) is from about 1,200 Dalton and about 50,000 Da, including from about 1,200, or from about 1,600, or from about 2,000, or from about 5,000, or from about 15,000, or from about 20,000, or from about 30,000, or from about 40,000 to about 50,000 total, or any suitable combination, sub-combination, range, or sub-range thereof. And each arm having a molecular weight of from about 300 Dalton to 12,500 Dalton, or from about 400 Da, or from about 500 Da, or from about 1,000 Dalton, or from about 1,250 Dalton, or from about 3,750 Dalton, or from about 5,000 Dalton, or from about 7,500 Dalton, or from about 10,000 Dalton, up to about 12,500 Dalton, or any suitable combination, sub-combination, range, or sub-range thereof. In some embodiments, each PEG unit has a molecular weight generally in the range of between about 1,250 and about and 2,500 Dalton, thus yielding a polymer having a PEG molecular weight of one of 5,000 Dalton (i.e., 5 k) or 10,000 Dalton (i.e., 10 k). Of course, other examples may include PEG units having a different molecular weight within the range from about 1.25 k to about 12.5 k.

In accordance with the various embodiments, the amount of the one or more shape memory polymer present in the composition is in a range about 0.5% to about 20%, or from about 1% to about 15%, or from about 1% to about 10%, or from about 5% to about 20%, or from about 10% to about 20%, or from about 15% to about 20%, or from about 1% to about 5% or from about 1% to about 2%, or any suitable combination, sub-combination, range, or sub-range thereof by weight, based on the weight of the composition. In some embodiments, the one or more shape memory polymer is present from at least 1%, or from at least 5%, or from at least 10%.

Thus, one or a combination of the shape memory polymers may be present, by weight, based on the total weight of the composition, each one or the combination present from about 0.5, 1, 2, 3, 4, 5, 6, 7, 8, 9, 10, 11, 12, 13, 14, 15, 16, 17, 18, 19 to about 20 weight percent, including increments and ranges therein and there between.

Adhering compositions may further include an oxidizing component. In some embodiments, the oxidizing component may be provided in a sub-composition that is applied after application of the adhering composition that comprises the shape memory polymer. According to such embodiments, the sub-composition includes an oxidizing agent or an agent that is rendered oxidizing upon chemical activation by a component in the adhering composition or by energy activation. In other embodiments, the oxidizing component may be provided as a reactive moiety in the adhering composition or in the shape memory polymer, the reactive moiety being rendered oxidizing upon chemical activation by a component in the adhering composition or by energy activation. In accordance with the various embodiments, the oxidizing agent serves to induce crosslinking among the monomer units of the shape memory polymer to form a durable network layer of shape memory polymer on the keratinous substrate to which it is applied.

Setting Composition

Setting compositions according to the disclosure have an acidic to neutral pH and comprise at least one metallic coordination agent and a carrier.

Metallic Ions or Metallic Oxidizing Agents

In accordance with the various embodiments, the compositions hereof include metallic coordination agents. The metallic coordination agents of the present invention include, but are not limited to, reagents comprising metal-containing compounds, for example compositions continuing transition metals, that are suitable for forming coordination complexes. In some embodiments, the metallic coordination agent may be chosen from iron (III) chloride. Other embodiments according to the disclosure include compositions comprising one or more of the metals selected from vanadium, aluminum, cobalt, nickel, manganese, copper and zinc.

In general, the metallic coordination agent is present in the composition in an amount that is represented as a molar ratio that is related to the amount of metal coordination active groups in the shape memory polymer. Thus, the metallic coordination agent is present typically in an amount that is in molar excess with respect to the number of metal coordinate active groups in the shape memory polymer.

Fixing Composition

In accordance with the various embodiments, the fixing composition has pH that is greater than the pH of the setting composition by at least $\Delta$ pH=1 and comprises at least a buffering agent to confer and a carrier.

Resetting Composition

In accordance with the various embodiments, the resetting composition comprises one of a chelating agent and a buffer that confers an acidic to neutral pH, and a carrier.

Buffers

In accordance with the various embodiments, the system comprising the various compositions includes various pH modifiers and/or buffering agents in order to achieve and maintain the appropriate pH for a composition. Examples of such reagents include, but are not limited to, acids such as citric and acetic acids, bases such as sodium and calcium hydroxide, buffers comprising mixtures of acids and their salts. An exemplary alkaline pH modifier comprises bicine, which has a pKa of 8.35 at 20° C. The pH modifiers and/or buffers are employed in the compositions of the present invention in an amount effective to achieve the desired pH level.

Carriers

In accordance with the various embodiments, the compositions hereof include suitable carriers. Carriers comprise one or more cosmetically acceptable ingredients useful in solubilizing, dispersing or delivering the compositions at the appropriate pH. In accordance with some embodiments, the carriers include one or more solvents comprising water. In some embodiments, the carriers include one or more glycols. Glycols may be selected from and include, by way of nonlimiting examples, glycerin, caprylyl glycol, propylene glycol, propanediol, polyethylene glycol, and other glycols, and combinations of these. In some embodiments, the carriers include one or more volatile solvents. Examples of volatile solvents include on or more of alcohols and low boiling silanes. In some embodiments, the carriers include one or more propellants. In some embodiments, the carriers include one or more oils, including volatile and nonvolatile oils. Carriers may be in the form of anhydrous or water-based forms, and may be formed as emulsions, including water in oil, oil in water, and silicone-based emulsions. Carriers may also be oil based. It will be appreciated that each of the compositions of the system as described in its various embodiments may include the same or different carriers. In some embodiments, the carriers include one or more of aesthetic components such as colorants, dyes, and perfumes. And carriers may include one or more optional ingredients as further included herein.

In accordance with the various embodiments, the amount of the one or more solvents that may be present in the composition ranges from about 0.1% to about 99%, or of from about 1% to about 80%, or from about 5% to about 75%, or from about 10% to about 60%, or from about 10% to about 50%, or any suitable combination, sub-combination, range, or sub-range thereof by weight, based on the weight of the composition.

Thus, one or a combination of solvents may be present, by weight, based on the total weight of the composition, each one or the combination present from about 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 to about 99 weight percent, including increments and ranges therein and there between.

In accordance with the various embodiments, the carrier is present in the compositions ranging from about 10% to about 99%, or of from about 20% to about 80%, or from about 5% to about 75%, or from about 10% to about 60%, or from about 10% to about 50%, or any suitable combination, sub-combination, range, or sub-range thereof by weight, based on the weight of the composition.

Chelating Agents

In accordance with the various embodiments, one or more compositions hereof include chelating agents. The chelating agents of the present invention include, but are not limited to, any chelating agents or sequestering agents. A chelating agent means and refers to a compound or ligand that can bind to a metal ion, usually through more than one ligand atom, to form a chelate.

In some embodiments, the chelating agent may be chosen from organic acids and salts thereof including carboxylic acids such as gluconic, citric and tartaric acids. The salts of the organic acids of the present invention may contain an organic or inorganic cation. In some embodiments, the chelating agent is chosen from mono-, di-, or poly-, amino- and hydroxy-carboxylic acids, mono-, di-, or poly-, amino- and hydroxy-sulfonic acids, and mono-, di-, or poly-, amino- and hydroxy-phosphonic acids.

Examples of suitable chelating agents include ethylene diamine tetraacetic acid (EDTA) and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; and N-2-hydroxyethyliminodiacetic acid and its salts. The salts may be chosen from salts with organic or inorganic cations. In one embodiment, the inorganic cation is chosen from potassium, sodium or lithium. However, the use of chelating agents that do not completely solubilize the metal ion and only form slightly soluble or sparingly soluble chelating agent-metal ion complexes is also within the practice of the invention.

In some particular embodiments, one or more chelating agent is selected from ethylenediaminetetraacetic acid (EDTA), tripotassium phosphate, trisodium phosphate, disodium silicate, dipotassium silicate, sodium phytate, tetrasodium etidronate, tetrasodium pyrophosphate, pentasodium ethylenediamine tetramethylene phosphonate, sodium staminate and combinations of these.

Depending on the nature of the chelating agent, the solubility in the reaction medium of the complex formed between the chelating agent and the metallic coordination agent may vary. A chelating agent-metallic coordination agent complex is considered by one of ordinary skill in the art to be soluble in the reaction medium.

In general, the chelating agent is present in the composition in an amount that is represented as a molar ratio that is related to the amount of metal coordination active groups and the amount of metallic coordination agent present. Thus, the chelating agent is present typically in an amount that is in molar excess with respect to the number of metal coordinate active groups in the shape memory polymer.

In accordance with the various embodiments, the amount of chelating agents present in the composition can be present in the composition according to the disclosure in a range from about 0.01% to about 5% by weight, or from about 0.05% to about 2% by weight, or from about 0.10% to about 1%, or from about 0.15% to about 0.5%, and from about 0.15% to about 0.2%, or any suitable combination, sub-combination, range, or sub-range thereof by weight, based on the weight of the composition.

Thus, one or a combination of chelating agents may be present, by weight, based on the total weight, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0 up to about 5.0 weight percent, including increments and ranges therein and there between.

Optional Ingredients

In accordance with the various embodiments, the compositions hereof may include other optional ingredients, as described below. The optional ingredients may be present in the carrier or otherwise present in any one or more of the compositions of the system.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups may be chosen from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then may comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and in some examples the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of ($C_6$-$C_{24}$)alkyl sulfates, ($C_6$-$C_{24}$) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from ($C_{10}$-$C_{20}$)alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

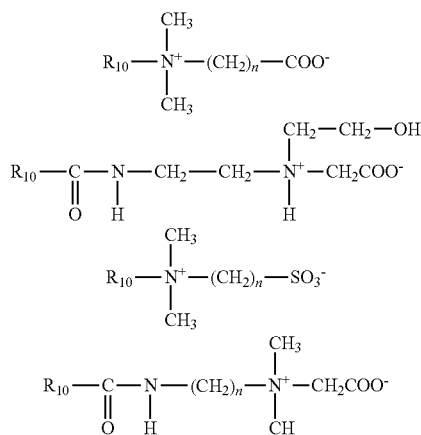

wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

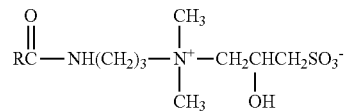

wherein
R is an alkyl group having 8-18 carbon atoms.
Useful alkylamphoacetates include those having the formula

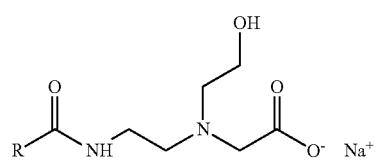

wherein

R is an alkyl group having 8-18 carbon atoms.

useful alkyl amphodiacetates include those having the formula

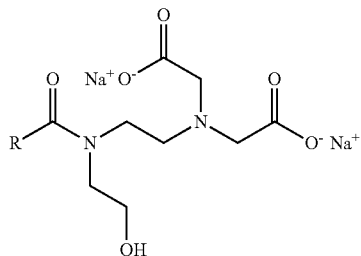

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may be chosen from polyoxyalkylenated or polyglycerolated nonionic surfactants. The oxyalkylene units are more particularly oxyethylene or oxypropylene units, or a combination thereof, and may be oxyethylene units.

In some cases, the nonionic surfactant may be selected from esters of polyols with fatty acids with a saturated or unsaturated chain containing for example from 8 to 24 carbon atoms, in some examples 12 to 22 carbon atoms, and alkoxylated derivatives thereof, in some examples with a number of alkyleneoxide of from 10 to 200, or from 10 to 100, such as glyceryl esters of a $C_8$-$C_{24}$, or $C_{12}$-$C_{22}$, fatty acid or acids and alkoxylated derivatives thereof, in some examples with a number of alkyleneoxide of from 10 to 200, and in some examples from 10 to 100; polyethylene glycol esters of a $C_8$-$C_{24}$, in some examples $C_{12}$-$C_{22}$, fatty acid or acids and alkoxylated derivatives thereof, in some examples with a number of alkyleneoxide of from 10 to 200, and in some examples from 10 to 100; sorbitol esters of a $C_8$-$C_{24}$, in some examples $C_{12}$-$C_{22}$, fatty acid or acids and alkoxylated derivatives thereof, in some examples with a number of alkyleneoxide of from 10 to 200, and in some examples from 10 to 100; sugar (sucrose, glucose, alkylglycose) esters of a $C_8$-$C_{24}$, in some examples $C_{12}$-$C_{22}$, fatty acid or acids and alkoxylated derivatives thereof, in some examples with a number of alkyleneoxide of from 10 to 200, and in some examples from 10 to 100; ethers of fatty alcohols; ethers of sugar and a $C_8$-$C_{24}$, in some examples $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Cationic Conditioning Agents

The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, am inopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR $C_{13}$-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the onee or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

Hydrating Agents

In accordance with the disclosure, in some embodiments, one or more hydrating agents may be present in one or more compositions of the system. Hydrating agents may be selected from and include any one or more synthetic and natural hydrating agents. Nonlimiting examples of hydrating agents include glycerin, squalane, sucrose, triacetin, monoethylene glycol, diethylene glycol, triethylene glycol, propylene glycol, butylene glycol, dipropylene glycol, diethylene glycol, hexylene glycol, glycol ethers such as monopropylene, dipropylene and tripropylene glycol alkyl ($C_1$-$C_4$)ethers, glycerol, xylitol, maltitol, sorbitol, pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In accordance with the various embodiments, the amount of any one or any combination of optional ingredients may be present in a composition in the range from about 1% to about 20%, or from about 1% to about 15%, or from about 1% to about 10%, or from about 2% to about 5%, or from about 5% to about 20%, or from about 10% to about 20%, or from about 15% to about 20%, or any suitable combination, sub-combination, range, or sub-range thereof by weight, based on the weight of the composition. In some embodiments, the one or more hydrating agents is present from at least 5%, or from at least 10%, or from at least 15%, or up to as much as 20%, or up to as much as 30%, or up to as much as 50%, or up to as much as 75%, or up to as much as 90%.

Thus, of any one or any combination of optional ingredients may be present, by weight, based on the total weight of the composition, each one or the combination present from about 1, 2, 3, 4, 5, 6, 7, 8, 9, 10, 11, 12, 13, 14, 15, 16, 17, 18, 19, 20, 30, 40, 50, 60, 70, 80 to about 90 weight percent, including increments and ranges therein and there between.

Optional Actives

In accordance with the disclosure, in some embodiments, one or more actives may be present in one or more compositions of the system. In some embodiments, actives used according to the disclosure may be selected from; antimicrobial components, including, but not limited to, caproyl glycine and sodium salicylate; antioxidants, including, but not limited to, phenolic compounds, such as chalcones, flavones, flavanones, flavanols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, phenolic terpenes, resveratrol, curcum in, pinoresinol, ferulic acid, hydroxytyrosol, cinnamic acid, caffeic acid, p-coumaric acid, baicalin, pine bark extract, ellagic acid; and vitamins and vitamin derivatives, such as panthenol, tocopherol, ascorbic acid; conditioning agents such as the silicone oil dimethicone, allantoin and dicaprylyl carbonate; clays such as kaolin; and combinations thereof. Although the aforementioned optional active components are given as an example, it will be appreciated that other optional components compatible with cosmetic applications known in the art may be used.

In accordance with the various embodiments, the amount of one or more actives, alone or in combination, present in the composition can be present in the composition according to the disclosure in a range from about 0.01% to about 20%, by weight, or from about 0.05% to about 15%, or from about 0.1% to about 10%, or from about 0.15% to about 5%, or from about 0.40% to about 4%, or from about 0.50% to about 2% by weight, or from about 1% to about 2%, or any suitable combination, sub-combination, range, or sub-range thereof by weight, based on the weight of the composition.

Thus, one or a combination of actives may be present, by weight, based on the total weight of the composition, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

In some representative embodiments, the compositors may comprise from 0% to about 3% surfactant. In some representative embodiments, the compositors may comprise from 0% to about 5% conditioning agent. In some representative embodiments, the compositors may comprise up to about 75% of oil in an oil-based composition. In some representative embodiments, the compositors may comprise from about 0.1% to about 3% of oil in a non-oil-based composition. In some representative embodiments, the compositors may comprise from 0% to about 1% of a binder. It will be appreciated that these optional embodiments are merely examples and are in no manner limiting of any of the possible compositions that can be formulated in accordance with the disclosure and comprise the inventive system and their embodiments hereof.

Packaging

In accordance with the various embodiments, the system components and compositions are provided in suitable packaging that includes a plurality of receptacles. For example, the packaging is provided to maintain separation between the compositions. In some embodiments, the packaging may include receptacles that contain at least one additional cosmetic composition, for example a cosmetic composition selected from a shampoo, a conditioner, a serum, a colorant, and combinations of these.

In one example, is an article of manufacture for cosmetic treatment of keratinous substrates, such as keratinous fibers, includes packaging that includes a plurality of separate receptacles, wherein at least one of the receptacles contains an adhering composition having an acidic to neutral pH, and including at least one shape memory polymer comprising a four-armed branched polyethylene glycol (PEG) based polymer that is functionalized with one or more metal-coordination active groups in a carrier. At least one of the receptacles contains a setting composition having an acidic to neutral pH and including one or more metallic coordination agent in a carrier. And at least one of the receptacles contains a fixing composition having a pH that is greater than the pH of the setting composition by at least $\Delta$ pH=1, which is in some embodiments alkaline as defined herein and as generally understood in the art. In some embodiments, the system further includes at least one additional receptacles containing a resetting composition that includes at least one of a chelating agent and a buffer that confers an acidic to neutral pH, and a carrier.

Raw Materials

Compositions as described in the representative embodiments according to the disclosure, and compositions as exemplified herein, include raw materials selected from commercially available materials, including, and all raw materials include active material present at 100% as added to a composition unless otherwise noted.

EXAMPLES

Example 1

Figure 2:
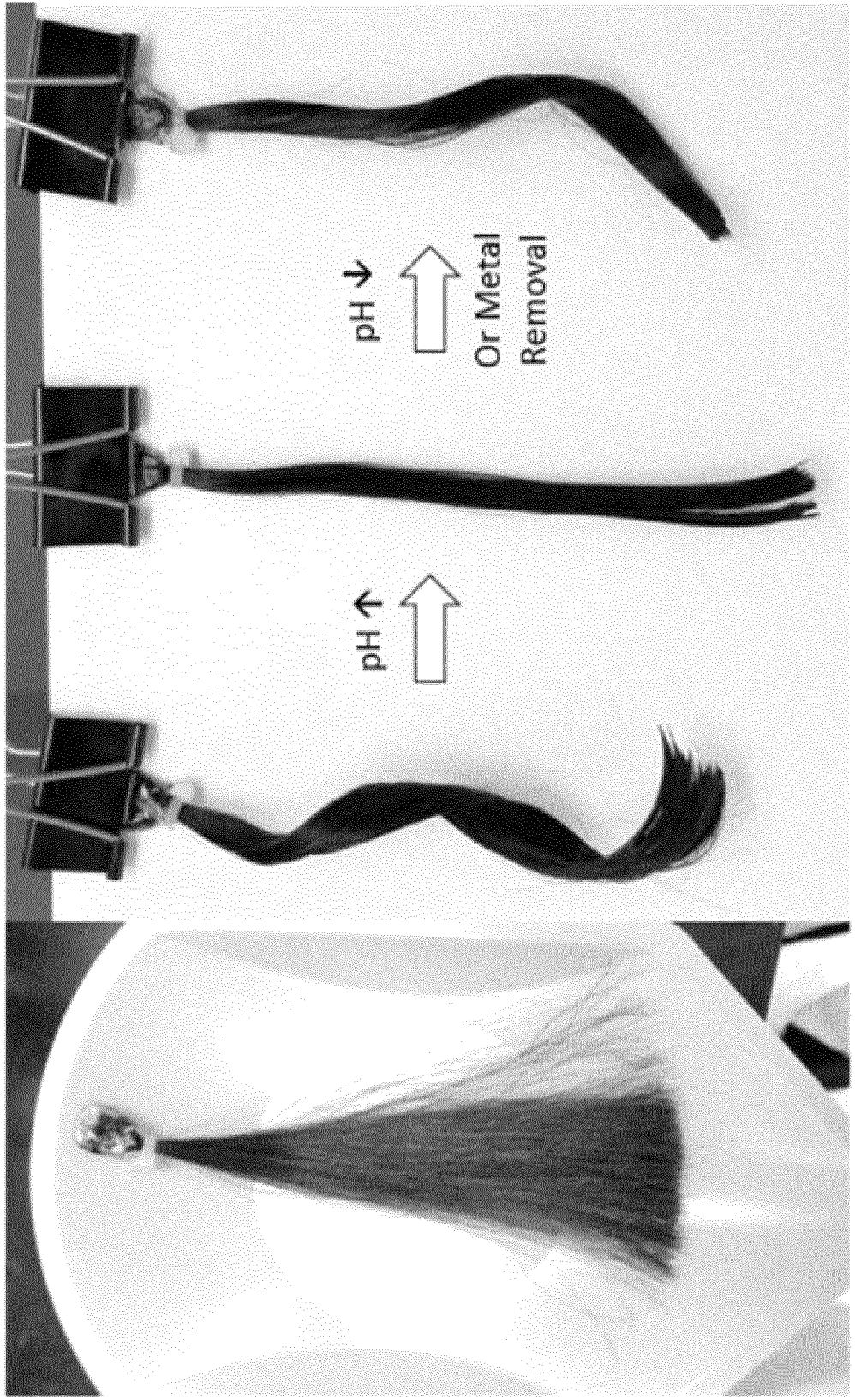
FIG. 2 shows images of a natural hair swatch test depicting the condition of hair subjected to a method of treatment according to the disclosure.

Studies on natural hair and hair swatches and demonstration of pH responsiveness for reprogrammable durable shaping of keratinous fibers Swatch shape-memory experiments (wet) showed hair shape can be set, reprogrammed and returned to the initial setting through one or more washing cycles. In the experiment, a swatch of naturally straight hair (first image in FIG. 2) was treated to confer a curl according to the regimen that included: (i) application of the adhering composition at an acid to neutral pH, (ii) wrapping the hair around a curling implement to confer a curled shape; (iii) application of the setting composition at an acid to neutral pH including an iron metallic coordination agent. The initial styling imparted was curling (second image in FIG. 2). Thereafter, the still wet curled hair was restyled by straightening, according to the regimen that included: (iv) pulling the hair straight between fingers followed by (v) application of the fixing composition at increased, alkaline pH to "lock" the reprogramed temporary style (third image in FIG. 2). Thereafter, the temporarily straightened hair was returned to the initial curled styling according to the regimen that included: (vi) rinsing with a resetting composition comprising the chelating agent, EDTA, to extract the coordinate bound metal (fourth image in FIG. 2). As shown, a degree of the initial curl was recovered. It will be appreciated that the resetting composition could have been provided in a carrier at an acidic to neutral pH.

In the example, the shape memory polymer used was a four-armed branched poly(ethylene glycol) (PEG) end-functionalized with a single DOPA, namely, $C-(PEG-DOPA)_4$. The chelating agent was EDTA, and the metallic coordination agent was iron(III) chloride.

Example 2

Coating deposition on hair through one shampooing cycle with a stripping shampoo (indicated by color change of polymer coating vs base 90% gray hair) In the experiment, a swatch of 90% gray hair was treated according to the regimen that included: (i) application of the adhering composition, (ii) application of the setting composition including an iron metallic coordination agent, (iii) drying for 4 hours at room temperature, (iv) washing with a stripping shampoo including a chelating agent followed by drying, (v) wrapping the hair around a curling implement (glass rod) to confer a curled shape, (vi) application of the setting composition including an iron metallic coordination agent, (vii) application of the fixing composition at increased pH to "lock" the style by holding the hair on the rod for 5 minutes, followed by (viii) drying for 4 hours at room temperature. The hair retained the cured shape.

In the example, the shape memory polymer used was a four-armed branched poly(ethylene glycol) (PEG) end-functionalized with a single DOPA, namely, C-(PEG-DOPA)$_4$ and the metallic coordination agent was iron(III) chloride.

Example 3

Single fiber shape-memory experiments, demonstrating the coating retains a curled shape and upon "de-activation" of temporary shape the initial shape is recovered.

Example 4

Figure 3:
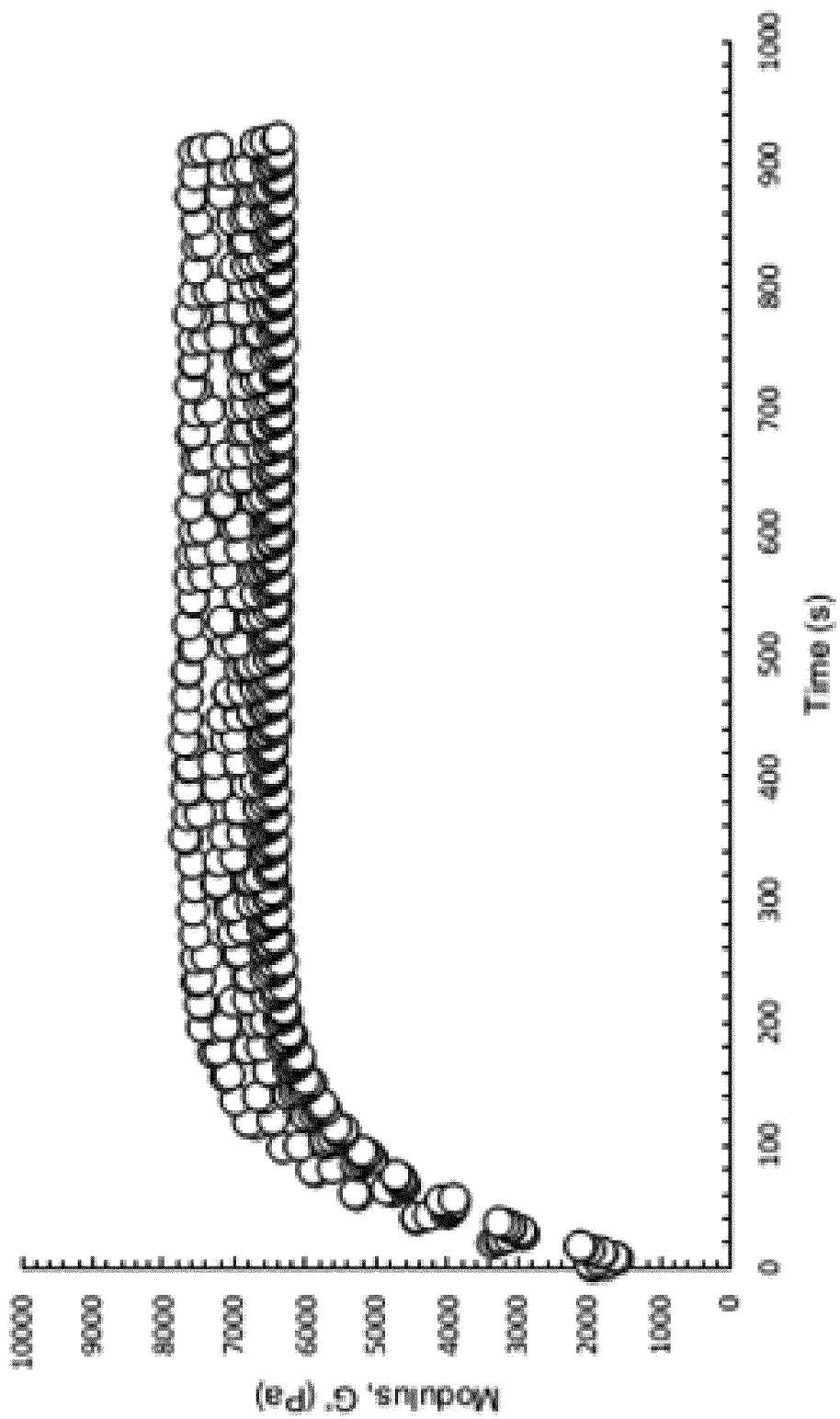
FIG. 3 shows a graph of change in modulus over time which demonstrates polymerization useful for forming a polymer coating on hair employing a 5 k total PEG molecular weight 4-armed PEG-DOPA (about 5,000 Dalton total, about 1,250 Dalton per arm)
Figure 4:
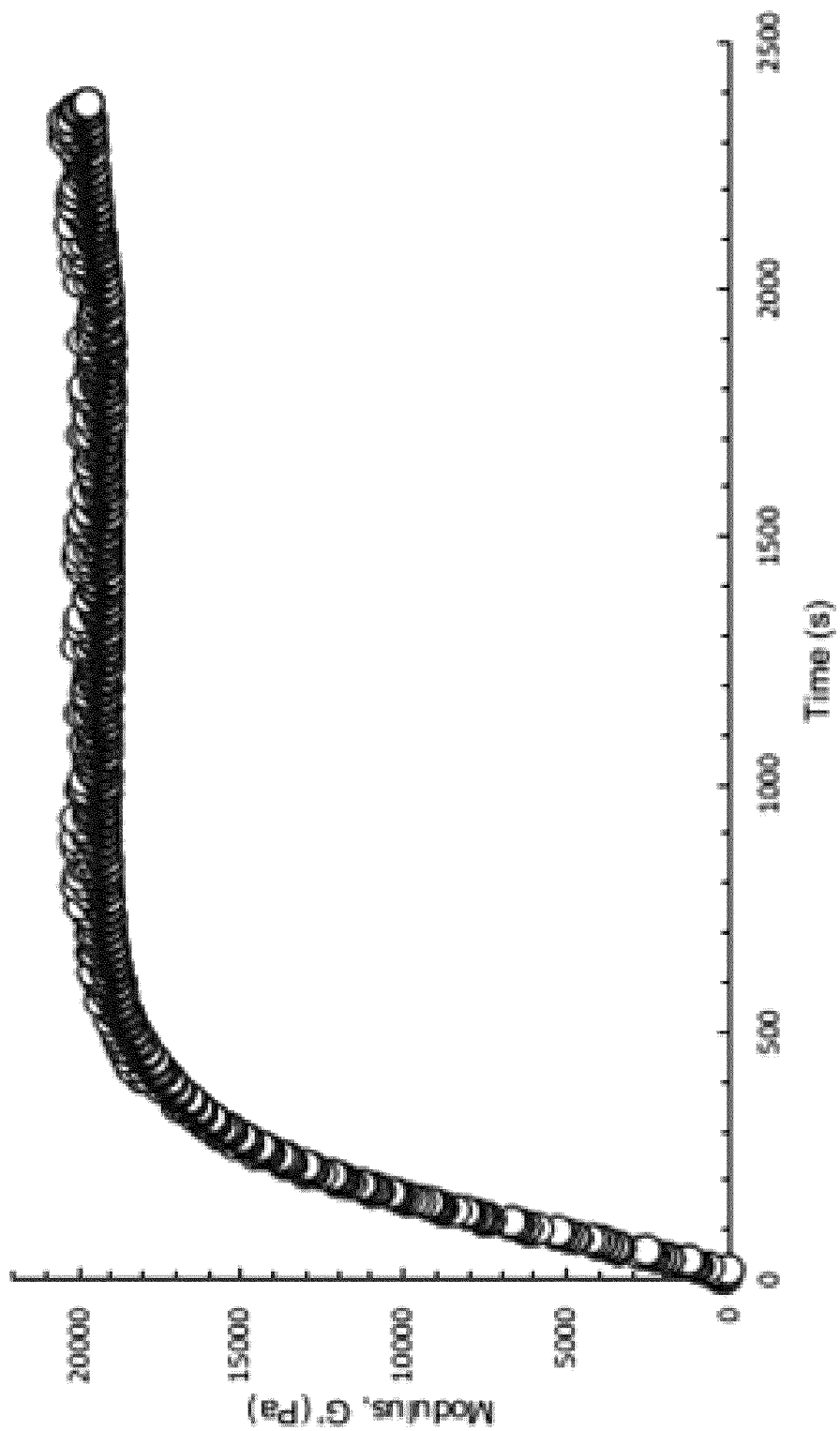
FIG. 4 shows a graph of change in modulus over time which demonstrates polymerization useful for forming a polymer coating on hair employing a 10 k total PEG molecular weight 4-armed PEG-DOPA (about 10,000 Dalton total, about 2,500 Dalton per arm).

Polymerization demonstration based on oscillatory rheology with 5 k molecular weight 4-arm PEG-DOPA (FIG. 3) and 10 k molecular weight 4-arm PEG-DOPA (FIG. 4).

Samples of four-armed PEG-DOPA were evaluated for polymerization to form a gel. Two samples of the polymer were used, one having a total PEG molecular weight of 5,000 Dalton (5,000 Dalton total, 1,250 Dalton per arm), and one having a total PEG molecular weight of 10,000 Dalton (10,000 Dalton total, 2,500 Dalton per arm). Referring now to the drawings, FIG. 3, shows polymerization of the 5 k PEG form of 4-armed PEG-DOPA, and FIG. 4 shows polymerization of the 10 k PEG form of 4-armed PEG-DOPA. Modulus, G', was determined by oscillatory rheology at different times as the FeCl$_3$ causes polymerization to occur. At each time point, multiple frequencies were tested, and plotted vertically, representing modulus determined at different frequencies of oscillation between 1 Hz and 10 Hz on the rheometer. The results show both 5 k and 10 k can be activated according to the instant disclosure by application of the setting composition that includes FeCl$_3$ to create coatings which can be formed on hair.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "from about 1% to about 10%, or from about 2% to about 8%, or from about 3% to about 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "from about 1% to about 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a certain embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. A cosmetic system for durable shaping of keratinous substrates, comprising:
   a) an adhering composition having an acidic to neutral pH, and comprising:
      i) at least one shape memory polymer comprising a four-armed branched polyethylene glycol (PEG)

based polymer that is functionalized with one or more metal-coordination active groups, and ii) a carrier;

b) a setting composition having an acidic pH, and comprising:
   i) one or more metallic coordination agent, and
   ii) a carrier; and c) a fixing composition having a pH that is greater than the pH of the setting composition by at least Δ pH=1, and comprising:
   i) a buffer, and
   ii) a carrier, wherein:
   the adhering composition is configured to mechanically coat the keratinous substrates;
   the setting composition is configured to form initial crosslinking of the at least one shape memory polymer of the adhering composition via the one or more metallic coordination agent; and
   the fixing composition is configured to lock the durable shaping by at least one of increasing covalent crosslinking of the at least one shape memory polymer of the adhering composition via the one or more metallic coordination agent or increasing ligand coordination from the initial crosslinking.

2. The system for durable shaping of keratinous substrates according to claim 1, further comprising an oxidizing agent that is present in one or more of (a) the adhering composition, (b) the setting composition, and a sub-composition, (a').

3. The system for durable shaping of keratinous substrates according to claim 2, wherein the oxidizing agent provides chemical crosslinking of monomer units of the shape memory polymer.

4. The system for durable shaping of keratinous substrates according to claim 1, wherein each of the compositions (a)-(c) is separately contained, and the cosmetic system, when applied to a keratinous substrate in a step-wise process corresponding with sequential application of each of (a), followed by (b), followed by (c), confers durable and reprogrammable durable shaping to the keratinous substrate.

5. The system for durable shaping of keratinous substrates according to claim 1, wherein the at least one polyethylene glycol (PEG) based polymer is functionalized by covalent crosslinking with one or more metal coordination active groups comprising a catechol.

6. The system for durable shaping of keratinous substrates according to claim 1, wherein the at least one polyethylene glycol (PEG) based polymer comprising a four-armed branched polyethylene glycol (PEG) based polymer comprises on each arm a metal-coordination active group comprising a 3,4-dihydroxy phenylalanine (DOPA)-based amino acid and a short peptide.

7. The system for durable shaping of keratinous substrates according to claim 1, wherein the total molecular weight of PEG in the polyethylene glycol (PEG) based polymer, accounting for the PEG portion of each arm, is from about 1,200 Dalton to about 50,000 Dalton, each arm having a molecular weight of from about 300 Dalton and about 12,500 Dalton.

8. The system for durable shaping of keratinous substrates according to claim 1, further comprising a resetting composition that comprises at least one of a chelating agent and a buffer that confers an acidic to neutral pH, and a carrier, wherein the pH of the resetting composition ranges from about 3 to about 6.

9. The system for durable shaping of keratinous substrates according to claim 8, wherein the one or more chelating agent is selected from the group consisting of ethylenediaminetetraacetic acid (EDTA), tripotassium phosphate, trisodium phosphate, disodium silicate, dipotassium silicate, sodium phytate, tetrasodium etidronate, tetrasodium pyrophosphate, pentasodium ethylenediamine tetramethylene phosphonate, sodium staminate, and combinations of these.

10. The system for durable shaping of keratinous substrates according to claim 1, wherein the one or more metallic coordination agent is selected from compounds suitable for forming coordination complexes comprising a metal selected from iron, vanadium, aluminum, cobalt, nickel, manganese, copper and zinc.

11. The system for durable shaping of keratinous substrates according to claim 10, wherein the one or more metallic coordination agent is a metal halide.

12. The system for durable shaping of keratinous substrates according to claim 1, wherein the one or more metallic coordination agent is iron chloride.

13. The system for durable shaping of keratinous substrates according to claim 6, wherein a DOPA-based amino acid is selected from dopamine, DOPA, dihydroxyhydrocinnamic acid, and 3,4-dihydroxyphenyl ethanol and the short peptide is selected from amino acids with polar side chains which are weakly to strongly basic.

14. The system for durable shaping of keratinous substrates according to claim 6, wherein the functionalized shape memory polymer is C-(PEG-DOPA)$_4$.

15. The system for durable shaping of keratinous substrates according to claim 1, wherein the pH of the adhering and setting compositions ranges from about 3 to about 6.

16. The system for durable shaping of keratinous substrates according to claim 1, wherein the pH of the fixing composition ranges from about 8 to about 11.

17. A process for durably shaping keratinous substrates, comprising:

a) treating the keratinous substrates with an adhering composition to mechanically coat the keratinous substrates, the adhering composition having an acidic to neutral pH and comprising a carrier and at least one shape memory polymer comprising a four-armed branched polyethylene glycol (PEG) based polymer that is functionalized with one or more metal-coordination active groups;

b) treating the keratinous substrates with a setting composition having an acidic pH and comprising a carrier and one or more metallic coordination agent to form initial crosslinking of the at least one shape memory polymer of the adhering composition via the one or more metallic coordination agent;

c) shaping the keratinous substrates either before or after step (b); and d) treating the keratinous substrates with a fixing composition having a pH that is greater than the pH of the setting composition by at least Δ pH=1 and comprising a carrier and a buffer to lock the shaping by at least one of increasing covalent crosslinking of the at least one shape memory polymer of the adhering composition via the one or more metallic coordination agent or increasing ligand coordination from the initial crosslinking, wherein the steps of treating provide durable and reprogrammable non-permanent shaping of the keratinous substrates.

18. The process according to claim 17, further comprising any one or more of the steps that include:
e) reshaping the keratinous substrates;
f) reshaping the keratinous substrates by the steps of wetting, reshaping the keratinous substrates, and treating the keratinous substrates with the fixing composition; and
g) reshaping the keratinous substrates by the steps of (e') treating the keratinous substrates with a resetting composition that comprises at least one of a chelating agent and a buffer that confers an acidic to neutral pH to release the shape imparted to the keratinous substrates, reshaping the keratinous substrates, and treating the keratinous substrates with the fixing composition.

19. An article of manufacture for durable and reversible reshaping of keratinous substrates, comprising packaging that includes a plurality of separate receptacles, the receptacles comprising:
i) at least one receptacle that contains an adhering composition having an acidic to neutral pH, the adhering composition comprising at least one shape memory polymer comprising a four-armed branched polyethylene glycol (PEG) based polymer that is functionalized with one or more metal-coordination active groups, and one or more chelating agent, in a carrier; and
ii) at least one receptacle that contains a setting composition having an acidic pH, and the setting composition comprising one or more metallic coordination agent in a carrier; and
iii) at least one receptacle that contains a fixing composition having a pH that is greater than the pH of the setting composition by at least $\Delta$ pH=1,
wherein:
the adhering composition is configured to mechanically coat the keratinous substrates;
the setting composition is configured to initially crosslink the at least one shape memory polymer of the adhering composition via the one or more metallic coordination agent; and
the fixing composition is configured to lock the durable shaping by at least one of increasing covalent crosslinking of the at least one shape memory polymer of the adhering composition via the one or more metallic coordination agent or increasing ligand coordination from the initial crosslinking.

20. The article of manufacture according to claim 19, wherein the receptacles are selected from blister packs, packets, tubes, vials, squeeze bottles, spray bottles, pressurized canisters, non-pressurized canisters, pump dispensers, and combinations of these, the article of manufacture comprising at least one additional receptacle that contains any one or more of: (a) a resetting composition comprising at least one of a chelating agent, a buffer that confers an acidic to neutral pH, and a carrier; and (b) a cosmetic composition selected from a shampoo, a conditioner, a serum, a colorant, and combinations of these.

* * * * *